United States Patent [19]

Steiner et al.

[11] 4,388,237

[45] Jun. 14, 1983

[54] 6(1-PIPERAZINYL), PIPERIDINO AND (1(HOMOPIPERAZINYL)11-CYANOMETHYLENE MORPHANTHRIDINES

[75] Inventors: Gerd Steiner, Kirchheim; Albrecht Franke, Wachenheim; Dieter Lenke; Hans-Juegen Teschendorf, both of Ludwigshafen; Wolfgang Worstmann, Gruenstadt; Horst Kreiskott, Wachenheim, all of Fed. Rep. of Germany

[73] Assignee: BASF Aktiengesellschaft, Fed. Rep. of Germany

[21] Appl. No.: 147,538

[22] Filed: May 7, 1980

[30] Foreign Application Priority Data

May 10, 1979 [DE] Fed. Rep. of Germany ....... 2918778

[51] Int. Cl.³ ................. C07D 403/04; C07D 403/06; C07D 401/04
[52] U.S. Cl. .......................... 260/239 BC; 260/243.3; 260/244.4; 260/239 D
[58] Field of Search ............. 260/243.3, 239 D, 244.4, 260/239 BC

[56] References Cited

U.S. PATENT DOCUMENTS

| 3,471,473 | 10/1969 | Walker | 260/239 D |
| 3,699,099 | 10/1972 | Drukker et al. | 260/239 D |
| 3,931,158 | 1/1976 | Freedman | 260/239 D |
| 4,045,445 | 8/1977 | Hardy et al. | 260/244.4 |

FOREIGN PATENT DOCUMENTS

| 2918832 | 5/1979 | Fed. Rep. of Germany ... 260/239 D |
| 834281 | 5/1960 | United Kingdom ............. 260/244.4 |

OTHER PUBLICATIONS

Hunziker et al. Helv. Chim. Acta 49 (1966), pp. 1433–1439.

*Primary Examiner*—Donald G. Daus
*Assistant Examiner*—D. B. Springer
*Attorney, Agent, or Firm*—Keil & Witherspoon

[57] ABSTRACT

6-Substituted 11-alkylene-morphanthridines, also referred to as 11-alkylene-dibenzo[b,e]-azepines, their pure cis- and trans-isomers, processes for their preparation, and therapeutic agents containing these compounds, which may be used as drugs, in particular neuroleptics, sedatives, hypnotics, analgesics, antidepressants or agents for treating Parkinson's syndrome.

16 Claims, No Drawings

6(1-PIPERAZINYL), PIPERIDINO AND (1(HOMOPIPERAZINYL))11-CYANOMETHYLENE MORPHANTHRIDINES

The present invention relates to 6-substituted 11-alkylene-morphanthridines, also referred to as 11-alkylene-dibenzo[b,e]-azepines, processes for their preparation, therapeutic agents containing these compounds, and their use as drugs.

It is known that tricyclic ring systems possessing a dibenzo structure joined to a central heterocyclic 7-membered ring, which may or may not possess a basic substituent, for example a N-methylpiperazine radical, can exhibit neuroleptic effects. Examples of such tricyclic compounds are N-methylpiperazine derivatives of dibenzo[b,e]-[1,4]-diazepines (Clozapine) or morphanthridines (Perlapine), as described, for example, in the review by J. Schmutz in Arzneimittelforschung 25 (1975), 712–720.

It is an object of the present invention to provide novel compounds which are more active and have lesser side effects.

We have found that this object is achieved by providing 6-substituted 11-alkylene-morphanthridines of the general formula I

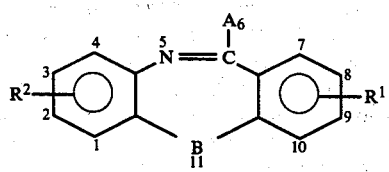

where $R^1$ and $R^2$ are hydrogen, halogen, especially fluorine, chlorine or bromine, alkyl of 1 to 3 carbon atoms or trifluoromethyl, and A is alkoxy —O—$R^3$, where $R^3$ is alkyl of 1 to 3 carbon atoms, cycloalkyl or cycloalkyl-methyl (where the cycloalkyl ring is of 3 to 6 carbon atoms and may or may not contain a nitrogen which is substituted by alkyl of 1 to 3 carbon atoms and may or may not be in the form of the N-oxide) or aminoalkyl of 2 to 7 carbon atoms, where the amine nitrogen may or may not be substituted by alkyl of 1 to 5 carbon atoms and may or may not form part of a 5-membered to 7-membered saturated ring, which ring may or may not contain a nitrogen (which may be substituted by alkyl of 1 to 3 carbon atoms and may or may not be in the form of a N-oxide) or an oxygen, as an additional hetero-atom, or A is amino —$NR^4R^5$, where $R^4$ and $R^5$ are identical or different and are hydrogen, alkyl of 1 to 5 carbon atoms, cycloalkyl or cycloalkylmethyl (where the cycloalkyl ring is of 3 to 6 carbon atoms and may or may not contain a nitrogen which is substituted by alkyl of 1 to 3 carbon atoms and may or may not be in the form of the N-oxide), hydroxyalkyl of 2 to 5 carbon atoms, aminoalkyl of 2 to 7 carbon atoms, where the amine nitrogen may or may not be substituted by lower alkyl of 1 to 5 carbon atoms, aralkyl of 7 to 9 carbon atoms or phenyl, and may or may not form part of a 5-membered to 7-membered saturated ring which may or may not contain a nitrogen (which is substituted by lower alkyl of 1 to 3 carbon atoms or hydroxyalkyl of 2 or 3 carbon atoms) or an oxygen, as a further heteroatom, or alkenyl of 2 to 5 carbon atoms or $R^4$ and $R^5$ together with the nitrogen atom by which they are joined form a 5-membered to 7-membered saturated ring which may or may not contain a nitrogen (which may or may not be substituted by alkyl of 1 to 3 carbon atoms, hydroxyalkyl of 2 or 3 carbon atoms, alkoxyalkyl, with alkyl and alkoxy each being of 1 to 3 carbon atoms, cycloalkyl or cycloalkyl-methyl, the cycloalkyl ring being of 3 to 7 carbon atoms, or alkynyl of 2 to 5 carbon atoms, and may or may not additionally be substituted by oxygen to form a N-oxide), or an oxygen, as an additional hetero-atom, and B is alkylene of the formula

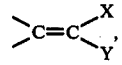

where X is hydrogen, lower alkyl of 1 to 3 carbon atoms or methoxy and Y is cyano, carboxamide (which may or may not be substituted at the amide nitrogen by 1 or two lower alkyl of 1 to 5 carbon atoms, which can also, together with the nitrogen, form a 5-membered to 7-membered ring), alkoxycarbonyl, where alkoxy is of 1 to 3 carbon atoms, methylcarbonyl, thiomethyl, sulfonomethyl, phenyl or pyridyl (which latter two may or may not be substituted in the nucleus by lower alkyl of 1 to 3 carbon atoms, halogen or cyano), the pure cis- and trans-isomers and the physiologically tolerated acid addition salts, and that these compounds exhibit valuable pharmacological properties.

$R^1$ and $R^2$ are preferably hydrogen, fluorine, chlorine, methyl or trifluoromethyl, hydrogen and methyl being particularly preferred.

Where A is alkoxy —$OR^3$, preferred meanings of $R^3$ are 2-dimethylamino-ethyl, 3-dimethylamino-propyl, piperidin-1-yl-ethyl, N-methyl-piperidin-3-yl-methyl, N-methyl-piperidin-2-yl-methyl, N-methyl-piperidin-4-yl and N-methyl-N-oxy-piperidin-3-yl-methyl, amongst which N-methyl-piperidin-3-yl-methyl, N-methyl-N-oxypiperidin-3-yl-methyl and 2-dimethylamino-ethyl are particularly preferred.

Examples of radicals A which are amine radicals

in which one of $R^4$ or $R^5$ is hydrogen, are: 2-aminoethyl, 2-dimethylamino-ethyl, 3-dimethylaminopropyl, 2-diethylamino-ethyl, 3-diethylamino-propyl, 4-dimethylamino-n-butyl, 2-hydroxyethyl, 2-piperidin-1-yl-ethyl, 2-pyrrolidin-1-yl-ethyl, 3-piperidin-1-yl-propyl, N-ethyl-pyrrolidin-2-yl-methyl, 2-morpholin-1-yl-ethyl, 2-piperazin-1-yl-ethyl, N-methyl-piperidin-3-yl-methyl, N-methyl-N-oxy-piperidin-3-yl-methyl, N-methyl-piperidin-2-yl-methyl, 1-methyl-2-morpholin-1-yl-ethyl, 2-(4-methyl-piperazin-1-yl)-ethyl, 3-(4-methyl-piperazin-1-yl)-propyl, 2-phenylamino-ethyl, 2-(N-methyl-N-benzylamino)-ethyl, 3-(N-methyl-N-benzyl-amino)-propyl, 1-methyl-2-(4-methyl-piperazin-1-yl)-ethyl and N-methylpiperidin-4-yl; examples where $R^4$ and $R^5$ form a 5-membered to 7-membered saturated ring, which may or may not contain a nitrogen or an oxygen as a further heteroatom are piperazinyl, homopiperazinyl, piperidinyl and morpholinyl radicals.

Particularly preferred radicals —$NR^4R^5$ are 4-methyl-piperazinyl, 4-methyl-4-oxy-piperazinyl, 4-(2-hydroxy)-ethyl-4-oxy-piperazinyl, 4-cyclopropyl-piperazinyl, 4-cyclopropylmethyl-piperazinyl, 4-propyn-2-ylpiperazinyl, 4-(2-hydroxy)-ethyl-piperazinyl, 4-ethylpiperazinyl and N-methyl-homopiperazinyl, and radicals —NHR$^4$, where R$^4$ is 2-dimethylaminoethyl or 2-piperidin-1-yl-ethyl.

Examples of radicals X are hydrogen, methyl, ethyl and methoxy.

The particularly preferred meaning of X is hydrogen.

Examples of radicals Y are cyano, carbamyl, N-methyl-carbamyl, N,N-dimethyl-carbamyl, piperidin-1-yl-carbonyl, methoxycarbonyl, methyl-carbonyl, thiomethyl, sulfonomethyl, phenyl, o-cyanophenyl and 4-pyridyl.

The particularly preferred meaning of Y is cyano.

The novel compounds, of the formula I, exist as cis- and trans-isomers Ia and Ib.

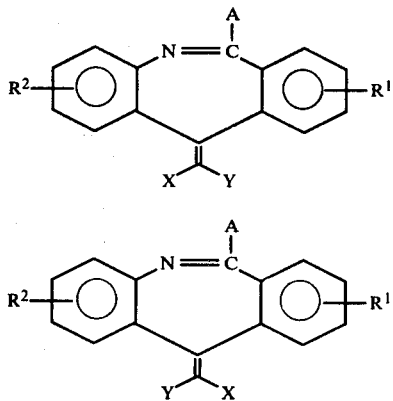

The cis- and trans-isomers can, if required, be separated, for example by fractional crystallization or by column chromatography. The appropriate structure may be allocated to the individual isomers by, for example, X-ray structural analysis, as is shown in the Examples.

In accordance with the above meanings, examples of particularly active compounds are the following: cis,-trans-11-cyanomethylene-6-(4-methyl-piperazin-1-yl)morphanthridine; cis-11-cyanomethylene-6-(4-methylpiperazin-1-yl)-morphanthridine; trans-11-cyanomethylene-6-(4-methyl-piperazin-1-yl)-morphanthridine; cis,trans-11-cyanomethylene-6-(4-methyl-4-oxy-piperazin-1-yl)morphanthridine; cis-11-cyanomethylene-6-(4-methyl-4-oxy-piperazin-1-yl)-morphanthridine; trans-11-cyanomethylene-6-(4-methyl-4-oxy-piperazin-1-yl)-morphanthridine; cis,trans-11-cyanomethylene-2-methyl-6-(4-methyl-piperazin-1-yl)-morphanthridine; cis,trans-11-cyanomethylene-3-methyl-6-(4-methyl-piperazin-1-yl)morphanthridine; cis-11-cyanomethylene-3-methyl-6-(4-methyl-piperazin-1-yl)-morphanthridine; trans-11-cyanomethylene-3-methyl-6-(4-methyl-piperazin-1-yl)-morphanthridine; cis,trans-11-cyanomethylene-6-(4-ethylpiperazin-1-yl)-morphanthridine; trans-11-cyanomethylene-6-(4-ethyl-piperazin-1-yl)-morphanthridine; cis,trans-11-cyanomethylene-6-(N'-methyl-homopiperazin-1-yl)morphanthridine and cis,trans-11-cyanomethylene-6-(2-piperidin-1-yl-ethylamino)-morphanthridine.

As is shown in the Examples, the separation of the cis- and trans-isomers can, in certain cases, be achieved without disproportionate effort.

The novel compounds of the formula I are prepared by a method wherein a compound of the formula II

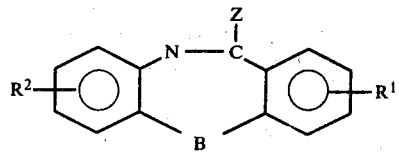

where R$^1$ and R$^2$ have the meanings given for formula I and in the alkylene radical B of the formula I X is hydrogen or methyl and Y is cyano, carboxamide (which may or may not be substituted at the amide nitrogen by one or two lower alkyl of 1 to 5 carbon atoms) or alkoxycarbonyl, where alkoxy is of 1 to 3 carbon atoms, and Z is a nucleofugic leaving group, is reacted with a nucleophilic agent AH, where A has the meanings given for formula I, and, if desired, the resulting compound is separated into the pure cis- and transisomers and/or is converted to the N-oxide and/or is converted to an addition salt with a physiologically tolerated acid.

Examples of suitable nucleofugic leaving groups Z are halogen, especially chlorine, sulfhydril, lower alkoxy, alkylthio or alkylamino of 1 to 3 carbon atoms, p-nitrobenzylthio and tosyloxy; of these, chlorine is particularly preferred.

The reaction is advantageously carried out in the presence of an excess of the amine or alcohol AH employed, which at the same time serves as a solvent and, where appropriate, serves as an acid-binding agent. An inert solvent, such as a cyclic saturated ether, especially tetrahydrofuran or dioxane, benzene or a benzene hydrocarbon, eg. xylene, mesitylene or decahydronaphthalene, may or may not be present. The reaction is as a rule carried out at from 80° to 150° C., preferably from 90° to 120° C., and is in general complete after from 3 to 10 hours. Excluding atmospheric oxygen and carrying out the reaction under an inert gas, for example under nitrogen, may or may not be advantageous.

Advantageously, the nucleophilic agent AH is employed in not less than 2-fold and up to 20-fold molar excess in the reaction.

If the nucleofugic group Z is alkylamino, the presence of a catalytic amount of a strong acid, for example p-toluenesulfonic acid or sulfuric acid, is advantageous.

The conversion of a compound of the formula I to the N-oxide is carried out in a conventional manner, advantageously using aqueous hydrogen peroxide (of 30% strength by weight) in solution in ethanol. The conversion of a compound to an addition salt with a physiologically tolerated acid is also carried out in a conventional manner.

The starting compounds of the formula II are obtained if a 5,6-dihydro-11-alkylene-morphanthridin-6-one of the formula III

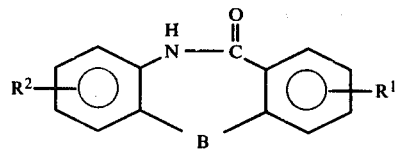

where R$^1$, R$^2$ and B have the meanings given for formula II and excess phosphorus oxychloride, which at the same time serves as the solvent, with or without a catalytic amount of N,N-dimethylaniline, are refluxed for from 3 to 6 hours in a conventional manner and the resulting imino-chloride, after distilling off the excess phosphorus oxychloride and working up in an aqueous two-phase system, is isolated by extraction with a chlorohydrocarbon, eg. chloroform or methylene chloride, after which it may or may not be reacted in a conventional manner with a further nucleophilic agent ZH, where Z has the meanings given for formula II.

The novel 5,6-dihydro-11-alkylene-morphanthridin-6-one of the formula III, where $R^1$ and $R^2$ have the meanings given for formula I, X in the alkylene radical B has the meanings given for formula I and Y is cyano, carboxamide or a lower carboxylic acid ester group as defined for formula II, is prepared by a carbonyl olefination reaction wherein a 5,6-dihydro-morphanthridine-6,11-dione of the formula IV

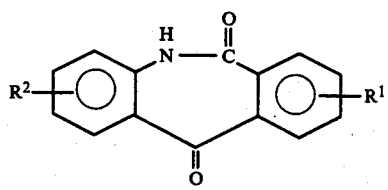

where $R^1$ and $R^2$ have the meanings given for formula I, is reacted with a phosphonate of the formula Va

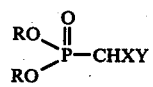

where R is alkyl of 1 to 3 carbon atoms and X and Y have the meanings given for formula III, under the conditions of a Wittig-Horner reaction, in an inert solvent, dimethylformamide being particularly preferred, in the presence of one mole equivalent of a base, preferably a sodium alcoholate or sodium hydride or sodium amide, at from 20° to 80° C., or is reacted with a phosphonium salt of the formula Vb

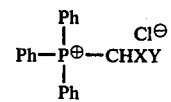

where Ph is phenyl and X and Y have the meanings given for formula Va, under the conditions of a conventional Wittig reaction, in an aprotic organic solvent, especially a saturated aliphatic or saturated cyclic ether, eg. diethyl ether, tetrahydrofuran or dioxane, or, preferably, in dimethylformamide, in the presence of one mole equivalent of a base, especially an alkali metal alcoholate, preferably sodium methylate or sodium ethylate, or sodium hydride, sodium amide or an organometallic compound, eg. butyl-lithium, at from 20° to 100° C.

Compounds of the formula III, where Y is methylcarbonyl, thiomethyl, sulfonomethyl, piperidin-1-yl-carbonyl or unsubstituted or substituted phenyl or pyridyl, or Y is cyano and X is not hydrogen, are advantageously prepared by converting the corresponding 5,6-dihydromorphanthridine-6,11-dione of the formula IV, by means of phosphorus oxychloride, to the imino-chloride of the formula VI, as described, for example, by F. Hunziker et al. in Helv. Chim. Acta 49 (1966), 1,433–1,439, reacting this imino-chloride with a nucleophilic agent AH in the manner described above to give a 6-substituted morphanthridin-11-one of the formula VII, and converting the latter, by a Wittig-Horner carbonyl olefination reaction, in the manner described above, to a compound of the formula I, as illustrated by the following set of equations:

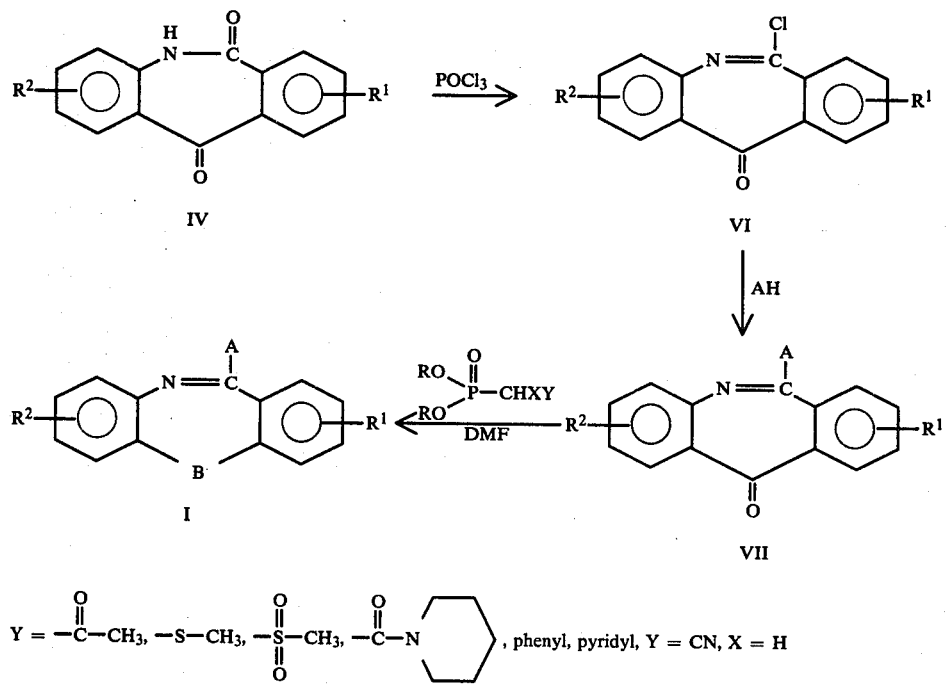

In a further process for the preparation of the compounds of the formula I, a compound of the formula VII

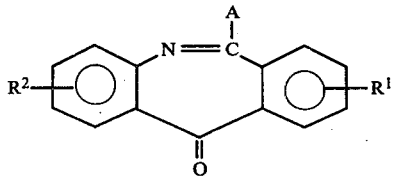

VII where $R^1$, $R^2$ and A have the meanings given for formula I, is reacted with a compound of the formula Vc

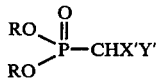

Vc where X' and Y' have the meanings given for X and Y in the radical B of the formula I and the R's are alkyl of 1 to 3 carbon atoms, under the conditions of a Wittig-Horner reaction, after which the resulting product may or may not be converted to the N-oxide and/or addition salt with a physiologically tolerated acid.

The conventional conditions of a Wittig-Horner reaction are to carry out the latter in an inert solvent, dimethylformamide being particularly preferred, in the presence of one mole equivalent of a base, preferably a sodium alcoholate, sodium hydride or sodium amide, at from 20° to 80° C.

This reaction is preferred for compounds where, in the end product of the formula I, Y is methylcarbonyl, thiomethyl, sulfonomethyl, piperidinylcarbonyl, phenyl or pyridyl and X is hydrogen, or Y is cyano and X is other than hydrogen.

In a further process for the preparation of compounds of the formula I, where $R^1$, $R^2$, A, and X in radical B, have the meanings given for formula I and Y is carboxamide, a 5,6-dihydro-11-carbalkoxymethylene-morphanthridin-6-one of the formula III, where Y is —COOR, R being alkyl of 1 to 3 carbon atoms, is hydrolyzed with alcoholic alkali metal hydroxide solution in a conventional manner, at from 40° to 90° C., to give the carboxylic acid, the resulting 5,6-dihydro-11-carboxymethylene-morphanthridin-6-one of the formula III, where Y is carboxyl, is reacted with thionyl chloride in a solvent at from 20° to 80° C. to give the carboxylic acid chloride and the latter is reacted with ammonia or an amine of the formula

where the R's are lower alkyl of 1 to 3 carbon atoms, advantageously in an aqueous medium or in an inert organic solvent, eg. a cyclic saturated ether, especially tetrahydrofuran or dioxane, advantageously at from 50° to 90° C., to give the corresponding 5,6-dihydro-11-carboxamidomethylene-morphanthridin-6-one.

The preparation of the imino-chloride of the formula II, and the subsequent substitution reaction with a nucleophilic agent AH in order to prepare the corresponding compound of the formula I, where Y is unsubstituted or substituted carboxamide, is carried out in the manner described above.

Some of the 5,6-dihydro-morphanthridine-6,11-diones of the formula IV are known from the literature (F. Hunziker et al., Helv. Chim. Acta 49 (1966), 1,433–1,439; L. H. Werner et al., J. Med. Chem. 8 (1965), 74–80; G. Caronna et al., Gazz. chim. ital. 84 (1954), 1,135–1,140); where they are not known, they can be obtained from the corresponding anthraquinones by ring enlargement, using a Schmidt reaction, as described in the Examples, or by halogen-substitution of the parent compound (E. Hardtmann and H. Ott, J. Org. Chem. 34 (1969), 2,244–2,248).

In addition to the compounds listed in the Examples, the following compounds may be given as examples: cis,trans-2-chloro-11-cyanomethylene-6-(4-methyl-piperazin-1-yl)-morphanthridine; cis,trans-11-cyanomethylene-8-methyl-6-(4-methyl-piperazin-1-yl)-morphanthridine; cis,trans-11-cyanomethylene-9-methyl-6-(4-methyl-piperazin-1-yl)-morphanthridine; cis,trans-11-cyanomethylene-2-trifluoromethyl-6-(4-methyl-piperazin-1-yl)-morphanthridine; cis,trans-11-cyanomethylene-3-trifluoromethyl-6-(4-methyl-piperazin-1-yl)-morphanthridine; cis,trans-11-cyanomethylene-3-fluoro-6-(4-methyl-piperazin-1-yl)-morphanthridine; cis,trans-11-cyanomethylene-8-fluoro-6-(4-methyl-piperazin-1-yl)-morphanthridine; cis,trans-11-cyanomethylene-6-(4-cyclopropyl-piperazin-1-yl)-morphanthridine; cis,trans-11-cyanomethylene-6-(4-cyclopropylmethyl-piperazin-1-yl)-morphanthridine and cis,trans-11-cyanomethylene-6-(4-propyn-2-yl-piperazin-1-yl)-morphanthridine.

The compounds according to the invention, of the formula I, are as a rule obtained in the form of yellowish or yellow crystals and can be purified by recrystallization from conventional organic solvents, preferably from a lower alcohol, eg. ethanol, or by column chromatography.

Where necessary, the product can be separated into the individual cis- and trans-isomers by fractional crystallization from a chlorohydrocarbon, preferably methylene chloride, a lower monohydric alcohol, preferably methanol or ethanol, or a saturated cycloaliphatic hydrocarbon, preferably cyclohexane, or by column chromatography, especially over silica gel, using methylene chloride or a mixture of methylene chloride and methanol in the volume ratio of from 99:1 to 85:15. The fractional crystallization is particularly preferentially carried out with two solvents.

A free 6-substituted 11-alkylene-morphanthridine of the formula I can be converted to the addition salt with a pharmacologically tolerated acid by a conventional method, preferably by adding one equivalent of the corresponding acid to a solution of the compound. Examples of pharmaceutically tolerated acids are hydrochloric acid, maleic acid and methanesulfonic acid; further examples may be found in J. Pharm. Sci., 66 (1977), 1–5.

According to the results of the pharmacological experiments, the compounds according to the invention can, by virtue of their sedative, apomorphine-antagonistic, analgesic, reserpine-antagonistic or anticholinergic action, be employed as neuroleptics, sedatives, hypnotics, analgesics, antidepressants or agents for treating Parkinson's syndrome.

The following methods were used to analyze the effects of the compounds:

1. Sedative effect

The substances are administered orally to groups of 4×3 or 8×3 female NMRI mice. The orientation hypermotility induced by a new environment is determined photoelectrically, 30 minutes after the administration of the substances, for a period of 30 minutes. The ED 50% is taken as the dose which reduces the orientation hypermotility by 50%, compared to untreated control animals.

2. Analgesic effect

The analgesic effect is determined by means of the D'Amour and Smith (1941) tail-flick method. In this, the substances are administered intraperitoneally to groups of 10 female NMRI mice. The pain reaction is triggered 30 minutes after administration. The reaction time, until the tail is flicked out of the way after exposure to a focused light beam, is measured.

The ED 100% is the dose which lengthens the reaction time by 100% compared to a control group.

3. Anti-cholinergic effect

A lethal dose (0.825 mg/kg) of Physostigmin is administered subcutaneously to groups of 10 female NMRI mice. The test substances are administered orally 30 minutes before administering the Physostigmin.

The ED 50% is the dose of substance which protects 50% of the animals against death from Physostigmin.

4. Apomorphine-antagonistic effect

Jaw motions are triggered in groups of 4-6 female Sprague-Dawley rats by subcutaneous administration of 1.5 mg of apomorphine/kg, and are recorded by means of implanted electrodes (Kubacki mandibulogram, 1978).

The ED 50% is the dose which reduces the number of jaw movements by 50% compared to untreated control animals.

5. Acute toxicity

The substances are administered intraperitoneally to groups of 5-10 female NMRI mice. The LD 50 is the dose which causes the death of 50% of the treated animals.

In these experiments (Table 1), strong sedative effects are observed with the compounds of Example 1 (cis-trans mixture and cis-isomer), Example 13a (cis-trans mixture and cis-isomer), Example 13b (cis-trans mixture), Example 31 (cis-trans mixture) and Example 38 (cis-trans mixture), which are of the order of magnitude of the effects of the reference substances Clozapin or Perlapin, or even exceed these.

An analgesic effect is found with the compound of Example 13a (cis-trans mixture and cis-isomer). The cis-isomer is substantially more active than Clozapin.

The anticholinergic effect observed from the Physostigmin antagonism manifests itself especially in the case of the compounds of Example 1 (cis-trans mixture and trans-isomer), Example 13b L (cis-trans mixture), Example 31 (cis-trans mixture and trans-isomer), Example 32 (cis-trans mixture) and Example 67 (cis-trans mixture and trans-isomer). In the case of Example 1 (cis-trans mixture), Example 13b (cis-trans mixture) and Example 31 (cis-trans mixture) it is found to be accompanied by relatively strong sedative effects (see above), similarly to the behavior of Clozapin.

Together with the above effects, most of the compounds also show an apomorphine-antagonistic effect which is typical of neuroleptics and which is also shown by the reference substances.

If the pharmacological properties of the cis-trans-isomer mixtures concerned are compared with those of the individual pure isomers, it is found, surprisingly, that there are not only quantitative but also qualitative differences so that novel and interesting combinations of effects are found for various substances.

The pattern of effects exhibited by the cis-trans mixture from Example 1 resembles that of the reference substance Clozapin. However, the mixture is more strongly sedative and anti-cholinergic and is not analgesically active. The apomorphine-antagonistic effect is somewhat weaker than that of Clozapin.

The cis-isomer of the compound of Example 1 is responsible for the sedative effect, and shows, relative to Clozapin, an approximately comparable anti-cholinergic effect and a lower apomorphine-antagonistic effect.

The trans-isomer of the compound of Example 1, on the other hand, particularly exhibits an anti-cholinergic and apomorphine-antagonistic effect. The sedative effect is very slight. This type of effect is novel and is clearly different from that of Clozapin and of Perlapin.

The trans-isomers of the compounds of Examples 13a, 31 and 67 also have little or no sedative effect but a stronger anti-cholinergic and apomorphine-antagonistic effect, and, as in the case of the trans-isomer of Example 1, differ, in their effects, from the corresponding isomer mixtures.

Another isomer mixture, namely that of Example 13a, has a high sedative activity (greater than that of Clozapin and Perlapin) with a moderate anti-cholinergic effect and a stronger analgesic effect. The cis-isomer is responsible for the strong sedative and strong analgesic effects. This compound, exhibiting a combination of sedative plus analgesic effect, with no anti-cholinergic effect and a weaker apomorphine-antagonistic effect than that of Clozapin and Perlapin, again offers a novel type of effect.

TABLE 1

| Compound No. | Geometrical isomerism | Sedative effect ED 50% | R.A.[1] | Analgesic effect ED 100% | R.A. | Apomorphine antagonism ED 50% | R.A. | Anti-chlolinergic effect ED 50% | R.A. | Toxicity LD 50 |
|---|---|---|---|---|---|---|---|---|---|---|
| 1 | cis-trans M[2] | 2.78 | 1.71 | 46.4 | 0.04 | 22 | 0.37 | 6.26 | 2.25 | 121 |
|  | cis-isomer | 1.98 | 2.39 | 31.6 | 0.07 | 46 | 0.17 | 17.4 | 0.81 | 147 |
|  | trans-isomer | >21.5 | <0.22 | >21.5 | <0.10 | 12 | 0.67 | 4.7 | 3.00 | 332 |
| 13a | cis-trans M | 0.804 | 5.90 | 5.17 | 0.40 | 35 | 0.23 | 31.2 | 0.45 | 178 |
|  | cis-isomer | 1.06 | 4.47 | 0.740 | 2.18 | 85 | 0.09 | 100 | 0.14 | 287 |
|  | trans-isomer | 33.6 | 0.14 | 68.1 | 0.03 | 19 | 0.42 | 12.3 | 1.15 |  |
| 13b | cis-trans M | 3.35 | 1.41 | 10.0 | 0.21 | 42 | 0.19 | 2.74 | 5.15 | 50.0 |
| 31 | cis-trans M | 3.34 | 1.42 | >10.0 | <0.21 | 43 | 0.19 | 7.80 | 1.81 | 100 |
|  | trans-isomer | >100 | >0.04 | >46.4 | <0.04 | 22 | 0.37 | 5.60 | 2.52 |  |
| 32 | cis-trans M | >21.5 | >0.22 | 46.4 | 0.04 | >100 | <0.08 | 5.49 | 2.57 | 69.8 |
| 38 | cis-trans M | 1.61 | 2.94 | >10.0 | <0.21 | 46 | 0.17 | >10.0 | <1.41 | 5.35 |
| 67 | cis-trans M | 14.3 | 0.33 | >46.4 | <0.04 | 85 | 0.09 | 1.98 | 7.12 | 464 |
|  | cis-isomer | 17.6 | 0.26 | >46.4 | <0.04 | >100 | <0.08 | 100 | 0.14 | 261 |
|  | trans-isomer | 100 | 0.04 | >100 | <0.02 | 25 | 0.32 | 3.74 | 3.77 | 559 |
| Clozapin |  | 4.74 | 1.00 | 2.08 | 1.00 | 8 | 1.00 | 14.1 | 1.00 | 215 |

TABLE 1-continued

| Compound No. | Geometrical isomerism | Sedative effect ED 50% | R.A.[1] | Analgesic effect ED 100% | R.A. | Apomorphine antagonism ED 50% | R.A. | Anti-chlolinergic effect ED 50% | R.A. | Toxicity LD 50 |
|---|---|---|---|---|---|---|---|---|---|---|
| Perlapin | | 2.05 | 2.31 | >21.5 | <0.10 | 22 | 0.37 | >21.5 | <0.66 | 215 |

[1] R.A. = relative activity
[2] M = mixture

Accordingly, the invention also relates to a therapeutic agent which contains a compound of the formula I, its pure cis- or trans-isomer or its pharmacologically tolerated addition salt with an acid, as the active ingredient, together with conventional carriers and diluents, and to the use of the novel compounds as drugs.

Therapeutic agents containing conventional carriers or diluents and the conventionally used technical auxiliaries may be prepared in a conventional manner, in accordance with the desired route of administration and in accordance with what is a suitable dosage unit to use. Suitable individual doses for man are from 10 to 100 mg.

The conventional pharmaceutical solid or liquid formulations suitable for administration, such as tablets, capsules, powders, granules, dragees or solutions, are employed. These are prepared in a conventional manner, in particular by mixing. For this purpose, the active compound may be formulated with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The resulting formulations normally contain from 0.001 to 99% by weight of the active compound.

The preferred pharmaceutical formulations are in a form suitable for oral administration. Such forms include, for example, tablets, film tablets, dragees, capsules, pills, powders, solutions, suspensions or depot forms. Parenteral formulations, such as injection solutions, may also be used. Further examples of combinations are suppositories.

The Examples which follow serve to illustrate the invention.

EXAMPLE 1 cis- and trans-11-Cyanomethylene-6-(4-methyl-piperazin-1-yl)-morphanthridine (a) 160 ml of phosphorus oxychloride and 3.5 ml of N,N-dimethylaniline are added to 20.0 g (81 millimoles) of 11-cyanomethylene-5,6-dihydro-morphanthridin-6-one (cis,trans-isomer mixture) and the batch is refluxed for 4 hours under nitrogen. The excess phosphorus oxychloride and dimethylaniline are then completely distilled off under reduced pressure from an oil pump, the residue is partitioned between methylene chloride and water, the aqueous phase is extracted twice more with methylene chloride, and the combined organic phases are thoroughly washed with dilute HCl and with water, dried and evaporated, giving 20.8 g (97%) of 6-chloro-11-cyanomethylene-morphanthridine, which is sufficiently pure for further reaction.

60 ml of N-methyl-piperazine are added to 20.8 g (79 millimoles) of 6-chloro-11-cyanomethylene-morphanthridine and the mixture is stirred for 3-5 hours at 110° C. under nitrogen. When it has cooled, the dark homogeneous reaction mixture is poured into ice water and the yellowish crude product, consisting of 11-cyanomethylene-6-(4-methyl-piperazin-1-yl)-morphanthridine, is filtered off, dried in an oven under reduced pressure and recrystallized from ethanol in the presence of active charcoal. 19.5 g (75%) of yellow 11-cyanomethylene-6-(4-methyl-piperazin-1-yl)-morphanthridine are obtained in the form of a cis,trans-isomer mixture, of melting point 148°-150° C.

To separate the cis- and trans-isomers, the isomer mixture is digested in about 80 ml of boiling methanol and the insoluble material is filtered off hot. This gives 3.1 g of a yellow solid which on the evidence of the thin layer chromatogram (silica gel, 85/15 toluene/methanol as the migrating agent) consists in the main of the non-polar isomer a. The filtrate is concentrated and the residue is taken up in a small amount of boiling methylene chloride, only just sufficient to dissolve all the material. On cooling, 3.0 g of a yellow product crystallize out; this is filtered off rapidly and washed with a very small amount of ice-cold methylene chloride. Thin layer chromatography indicates a very good degree of enrichment in polar isomer b.

By repeating these two successive operations several times, about 10-11 g fractions of each of the highly enriched isomers, coded a and b, are obtained, and these are then recrystallized once or twice more from ethanol.

Pure isomer a is obtained in the form of yellow rectangular flakes of melting point 210°-212° C., and pure isomer b in the form of yellow sharp needles of melting point 182°-184° C.

X-ray structural analysis indicates that a is the cis-isomer and b the trans-isomer of 11-cyanomethylene-6-(4-methylene-piperazin-1-yl)-morphanthridine.

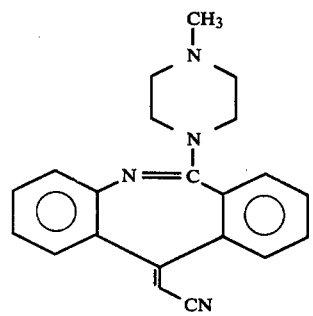

-continued

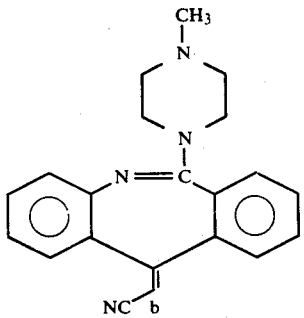

The intermediate 11-cyanomethylene-5,6-dihydromorphanthridin-6-one is prepared as follows by carrying out a carbonyl olefination of 5,6-dihydro-morphanthridine-6,11-dione, using a Wittig-Horner reaction or a conventional Wittig synthesis.

(b) 30.0 g (135 millimoles) of 5,6-dihydro-morphanthridine-6,11-dione are dissolved in 300 ml of dimethylformamide and the solution is stirred under nitrogen. 35.4 g (200 millimoles) of diethyl cyanomethyl-phosphonate and 35.0 g (200 millimoles) of a 30% strength solution of sodium methylate in 100 ml of dimethylformamide are then slowly added dropwise at the same time. An increase in the depth of color, and a rise in temperature, indicate that the Wittig reaction has started. After stirring the mixture for a further 12 hours at room temperature, the reaction product is poured into ice water and the solid which has precipitated is filtered off. The crude product is thoroughly washed with water, dried and recrystallized from ethanol. Yield: 32.5 g (98%) of 11-cyanomethylene-5,6-dihydromorphanthridin-6-one, in the form of colorless crystals of melting point 221°–223° C.

(c) Conventional Wittig process: triphenylcyanomethyl-phosphonium chloride is introduced into dimethylformamide, 1 mole equivalent of a 30% strength sodium methylate solution is then added dropwise, or 1 mole equivalent of sodium hydride is added, and finally 1 mole equivalent of a solution of 5,6-dihydro-morphanthridine-6,11-dione in dimethylformamide is also introduced. The reaction mixture is then stirred for from 5 to 8 hours at 50°–80° C., then poured into ice water, and extracted repeatedly with methylene chloride. The organic phase is dried, the solvent is removed, and the crude product is recrystallized from ethanol. Yield: 67% of colorless crystals of melting point 220°–222° C.

EXAMPLE 2 cis,trans-11-Carbomethoxymethylene-6-(4-methyl-piperazin-1-yl)-morphanthridine

11-Carbomethoxymethylene-5,6-dihydro-morphanthridin-6-one is prepared by the method of Example 1b from 5,6-dihydro-morphanthridine-6,11-dione and diethyl carbomethoxymethyl-phosphonate as the Wittig-Horner reagent. Yield 96%, melting point 184°–185° C.

11-Carbomethoxymethylene-6-(4-methyl-piperazin-1-yl)-morphanthridine is obtained by method 1a. The crude product is purified by column chromatography (silica gel, with methylene chloride as the migrating agent). The cis,trans-isomer mixture is obtained, in 45% yield, as yellow crystals of melting point 75°–79° C.

EXAMPLE 3 cis,trans-11-Carboxamidomethylene-6-(4-methyl-piperazin-1-yl)-morphanthridine

Variant a:

The intermediate 11-carboxamidomethylene-5,6-dihydro-morphanthridin-6-one is prepared by the method of Example 1b, using diethyl-phosphonoacetamide (prepared by an Arbuzov reaction from triethyl phosphite and chloroacetamide), the temperature at which the mixture is subsequently stirred being increased to 50°–80° C.; instead of sodium methylate, sodium hydride suspended in DMF may advantageously be used. Melting point of the product 283°–288° C.

11-Carboxamidomethylene-6-(4-methyl-piperazin-1-yl)-morphanthridine is prepared by the method of Example 1a. After recrystallization from ethanol, the cis, trans-isomer mixture is obtained, in 65% yield, in the form of yellow crystals of melting point 185°–193° C.

Variant b:

The compound may also be obtained as follows:

1. 20 ml of 10% strength sodium hydroxide solution are added to 20 g (72 millimoles) of 11-carbomethoxymethylene-5,6-dihydro-morphanthridin-6-one in 20 ml of ethanol and the mixture is briefly heated to 60° C. and then stirred for 2 hours at room temperature. It is filtered, the filtrate is acidified with 10% strength hydrochloric acid, and the crystals which have precipitated are filtered off and thoroughly washed with water. 19.0 g (99%) of 5,6-dihydro-morphanthridin-6-one-11-methylene-carboxylic acid are obtained; melting point 273°–275° C.

2. 80 ml of thionyl chloride are added to 6.0 g (23 millimoles) of 5,6-dihydro-morphanthridin-6-one-11-methylene-carboxylic acid and the mixture is stirred at room temperature. Solution occurs within 1 hour. After stirring the mixture for a further hour, the thionyl chloride is stripped off under reduced pressure from an oil pump, the residue is taken up in a small amount of toluene and the solvent is again completely stripped off. The 5,6-dihydro-morphanthridin-6-one-11-methylene-carboxylic acid chloride which remains is sufficiently pure to be reacted further. The residue is taken up in 200 ml of concentrated ammonia, ethanol is added, whilst stirring, until all has dissolved, and the mixture is heated for 2–3 hours at 90° C. It is cooled and concentrated to ¼ of its volume, and the solids which have precipitated are filtered off. 4.8 g (79%) of 11-carboxamidomethylene-5,6-dihydromorphanthridin-6-one are obtained; melting point 284°–288° C.

3. For the further conversion to the end product, see Example 3a.

EXAMPLE 4 cis,trans-11-N-Methyl-carboxamidomethylene-6-(4-methylpiperazin-1-yl)-morphanthridine The compound is prepared by a method similar to Example 3b: 200 ml of 40% strength aqueous methylamine solution are added to 5.0 g (18 millimoles) of 5,6-dihydro-morphanthridin-6-one-11-methylene-carboxylic acid chloride and the mixture is stirred for 2 hours at 80°–90° C. It is worked up as described above, giving 4.7 g (94%) of 11-N-methylcarboxamidomethylene-5,6-dihydro-morphanthridin-6-one; melting point 250°–253° C.

cis,trans-11-N-Methyl-carboxamidomethylene-6-(4-methyl-piperazin-1-yl)-morphanthridine, prepared by a method similar to the preceding Example, is purified by column chromatography (silica gel, with 95/5 methylene chloride/methanol as the migrating agent). Yellow crystals, of melting point 118°–124° C.

EXAMPLE 5 cis,trans-11-N,N-Dimethyl-carboxamidomethylene-6-(4-methyl-piperazin-1-yl)-morphanthridine . $H_2O$ 11-N,N-Dimethyl-carboxamidomethylene-5,6-dihydromorphanthridin-6-one, of melting point 89°–94° C., is prepared by a method similar to Example 4, using a 40% strength aqueous dimethylamine solution.

The end product is prepared, and purified, by a method similar to Example 4. Yellow crystals of melting point 161°–163° C.

EXAMPLE 6 cis,trans-11-(α-Methyl)-cyanomethylene-6-(4-methyl-piperazin-1-yl)-morphanthridine . ½ $H_2O$ (a) The compound is prepared by a method similar to Example 1a. After purification by means of column chromatography (silica gel, and 95/5 methylene chloride/methanol), yellow crystals of melting point 96°–98° C. are obtained.

The intermediate 11-(α-methyl)-cyanomethylene-5,6-dihydro-morphanthridin-6-one is prepared by a method similar to Example 1b, by carbonyl olefination with diethyl 1-cyano-ethyl-phosphonate (obtainable by an Arbuzov reaction from triethyl phosphite and 2-bromo-propionitrile, or by the method of D. L. Comins et al., Synthesis (1978), 309), advantageously using sodium hydride instead of sodium ethylate, and allowing 4–6 hours at 80° C. Melting point 256°–260° C.

(b) The phosphonate is prepared by in situ alkylation, as described by W. S. Wadsworth and W. D. Emmons, J. Amer. Chem. Soc. 83 (1961), 1,733, and A. E. Arbuzov et al., J. Russ. Phys. Chem. Soc. 61 (1929), 623.

28 millimoles of sodium hydride (55% strength in mineral oil) are added, in portions, to 5.0 g (28 millimoles) of diethyl cyanomethyl-phosphonate in 25 ml of dimethylformamide, whilst stirring vigorously under nitrogen as a blanketing gas; the mixture is then stirred for a further 15 minutes, until a clear solution is obtained. 4.0 g (28 millimoles) of methyl iodide are then added dropwise whilst keeping the temperature below 30° C. by cooling. Stirring is continued for 4 hours at room temperature (during which sodium iodide precipitates), a further 28 millimoles of sodium hydride are then added and finally 8.5 g (28 millimoles) of 6-(4-methyl-piperazin-1-yl)-morphanthridin-11-one (see Example 15) in 70 ml of dimethylformamide are introduced dropwise. After stirring for a further 5–8 hours at 50°–80° C., the mixture is poured into ice-water and the solid which precipitates is filtered off and is copiously washed with water. It is then subjected to column chromatography (silica gel and 95/5 methylene chloride/methanol), and cis,trans-11-(α-methyl)-cyanomethylene-6-(4-methylpiperazin-1-yl)-morphanthridine.½$H_2O$, of melting point 94°–98° C., is isolated.

EXAMPLE 7 cis,trans-11-(α-Ethyl)-cyanomethylene-6-(4-methylpiperazin-1-yl)-morphanthridine The compound is prepared by a method similar to Variant b of Example 6, using ethyl iodide. Yellow crystals, of melting point 78°–82° C.

EXAMPLE 8 cis,trans-9-Chloro-11-cyanomethylene-6-(4-methyl-piperazin-1-yl)-morphanthridine (a) 9-Amino-5,6-dihydro-morphanthridine-6,11-dione 20.0 g (90 millimoles) of 2-aminoanthraquinone are introduced into a mixture of 96 ml of concentrated sulfuric acid and 32 ml of methylene chloride and dissolved at room temperature, whilst stirring. 6.8 g (105 millimoles) of sodium azide are introduced in portions, over 5 hours, into the above reaction mixture at 20° C. (using external cooling by means of a waterbath). The reaction mixture is stirred overnight at room temperature and is then cautiously poured into 3 liters of ice water. The pH of the aqueous mixture is brought to 9 with concentrated sodium hydroxide solution and the solids which have precipitated are filtered off and washed with a copious amount of water. The crude product is dried in an oven under reduced pressure at 70° C.

In order to separate the isomer mixture—which, on the evidence of the 270 MHz $^1$H-NMR spectrum contains 4 amino-isomers—the mixture is digested in 1 liter of boiling ethanol and the insoluble material (accounting for about ¼ of the total) is filtered off hot. 4.5 g (21%) of highly enriched 9-amino-5,6-dihydro-morphanthridine-6,11-dione of melting point 295°–297° C. are obtained; the pure isomer is obtained by recrystallizing from about 200 ml of a 3:1 ethanol/dimethylformamide mixture, in the presence of active charcoal. The position of the amino group follows from the X-ray structural analysis of the end product (see below).

$^1$H-NMR (270 MHz, $D_6DMSO$): δ=6.30 (s, $NH_2$), 6.97 (d, 1H), 7.01 (s, 1H), 7.20 (t, 1H), 7.37 (d, 1H), 7.59 (t, 1H), 7.72 (d, 1H), 7.98 (d, 1H), 10.70 (s, NH).

The 2-, 3- and 8-amino-5,6-dihydro-morphanthridine-6,11-diones which remain in the ethanolic mother liquor can be enriched by fractional crystallization. The fractions are in each case analyzed by recording the 270 MHz $^1$H-NMR spectrum.

(b) 9-Chloro-5,6-dihydro-morphanthridine-6,11-dione 3.0 g (12.6 millimoles) of 9-amino-5,6-dihydromorphanthridine-6,11-dione are introduced into a mixture of 120 ml of water and 120 ml of concentrated hydrochloric acid. A solution of 0.87 g (12.6 millimoles) of sodium nitrite in 10 ml of $H_2O$ is added dropwise at 0°–5° C., with thorough stirring, and stirring is then continued for 2.5 hours at the same temperature. A small amount of urea is then added to destroy the excess nitrous acid, after which 120 millimoles of a freshly prepared Cu(I) chloride catalyst in concentrated hydrochloric acid are added, resulting in evolution of nitrogen. The mixture is stirred for a further 30 minutes at room temperature and is then heated for 1 hour at 100° C., with constant stirring. After it has cooled, the reaction mixture is poured into ice water and is extracted with three×300 ml of methylene chloride. The combined organic phases are then washed with water, dried and concentrated. 1.9 g of 9-chloro-5,6-dihydro-morphanthridine-6,11-dione are obtained; melting point 265°–267° C.

(c)

Further reaction to give the end product, by a method similar to Example 1:

cis,trans-9-Chloro-11-cyanomethylene-5,6-dihydromorphanthridin-6-one is obtained by a method similar to Example 1b. Melting point 250°–255° C.

cis,trans-9-Chloro-11-cyanomethylene-6-(4-methyl-piperazin-1-yl)-morphanthridine.·½H$_2$O is obtained by a method similar to Example 1a. Melting point 90°–95° C.

To separate the cis,trans-isomers, the product is subjected to fractional recrystallization from ethanol. The pure cis-isomer, which is the more sparingly soluble fraction, crystallizes out first. This isomer is the non-polar component on a silica gel thin layer plate, using 85/15 toluene/methanol as the migrating agent. Melting point: 173°–174° C.

The 9-position of the chlorine is confirmed by X-ray structural analysis of the cis-isomer.

(d) cis,trans-3- and 8-chloro-11-cyanomethylene-6-(4-methyl-piperazin-1-yl)-morphanthridine The monochloro-5,6-dihydro-morphanthridine-6,11-dione isomer mixture (essentially containing 3 differently chlorinated isomers), employed as the starting material and obtained by ring enlargement of 2-chloro-anthraquinone, using the method of L. H. Werner et al., J. Med. Chem. 8, (1965), 74, proved impossible to separate by fractional crystallization, contrary to the statement by L. H. Werner et al., loc. cit. (It is true that fractions with similar melting points were obtained, as stated by L. H. Werner et al., loc. cit., but on the evidence of the 270 MHz $^1$H-NMR spectrum these fractions were each mixtures of 2 or 3 isomers). Hence, the further reactions were carried out with the isomer mixture and a separation was only performed on the product obtained in the last stage.

Synthesis by a method similar to Example 1:

The carbonyl olefination gives a monochloro-11-cyanomethylene-5,6-dihydro-morphanthridin-6-one isomer mixture of melting point 148°–151° C. The end product, consisting of 8 isomers (as indicated by thin layer chromatography on silica gel, using 85/15 toluene/methanol; doubling due to cis,trans-isomerism), and having a melting point of 95°–99° C., is recrystallized from ethanol and then subjected to column chromatography (silica gel, 95/5 methylene chloride/methanol) to produce enrichment of the individual fractions. This allows isolation, and characterization, of the cis, trans-2- and -9-chloro-11-cyanomethylene-6-(4-methylpiperazin-1-yl)-morphanthridine isomers, described in Examples 11 and 8c, and constituting the polar and less polar constituents respectively.

The remaining cis,trans-3- and -8-chloro-11-cyanomethylene-6-(4-methyl-piperazin-1-yl)-morphanthridine isomers, which still remain, are obtained in an enriched form as further fractions. Yellow crystals of melting point 95°–98° C.

EXAMPLE 9 cis,trans-4-Chloro-11-cyanomethylene-6-(4-methylpiperazin-1-yl)-morphanthridine.·½H$_2$O The compound is prepared by a method similar to Example 1. After column chromatography (silica gel, 95/5 methylene chloride/methanol), yellow crystals of melting point 90°–95° C. are obtained. The starting material used is the ring enlargement product of 1-chloroanthraquinone, prepared by the method of L. H. Werner et al., J. Med. Chem. 8 (1965), 74, which was separated by column chromatography (silica gel, 95/5 methylene chloride/methanol), the polar component having a melting point of 196°–198° C.

The 4-position of the chlorine was not separately confirmed. The Wittig reaction gives 4-chloro-11-cyanomethylene-5,6-dihydro-morphanthridin-6-one, of melting point 231°–233° C.

EXAMPLE 10 cis,trans-7-Chloro-11-cyanomethylene-6-(4-methylpiperazin-1-yl)-morphanthridine

The compound is prepared by a method similar to Example 1. Yellow crystals of melting point 219°–221° C.

The starting material used is the non-polar component of monochloro-5,6-dihydro-morphanthridine-6,11-dione (see Example 9), of melting point 269°–270° C.

The 7-position of the chlorine was not confirmed. Carbonyl olefination gives 7-chloro-11-cyanomethylene-5,6-dihydro-morphanthridin-6-one, of melting point 207°–210° C.

EXAMPLE 11 cis,trans-2-Chloro-11-cyanomethylene-6-(4-methylpiperazin-1-yl)-morphanthridine.·½H$_2$O The compound is prepared by a method similar to Example 1. Yellow crystals of melting point 157°–162° C.

The starting material used is 2-chloro-5,6-dihydro-morphanthridine-6,11-dione (E. Hardtmann and H. Ott, J. Org. Chem. 34 (1969), 2,244–2,248).

Carbonyl olefination by a method similar to Example 1b gives 2-chloro-11-cyanomethylene-5,6-dihydromorphanthridin-6-one, of melting point 270° C.

EXAMPLE 12 cis,trans-9-Fluoro-11-cyanomethylene-6-(4-methylpiperazin-1-yl)-morphanthridine (a) 3.6 g (15.1 millimoles) of 9-amino-5,6-dihydromorphanthridine-6,11-dione (Example 8a) are suspended in a mixture of 100 ml of water and 100 ml of concentrated hydrochloric acid. After the mixture has cooled to 0°–5° C., a solution of 1.06 g (15.1 millimoles) of sodium nitrile in 20 ml of water is added dropwise, with thorough stirring. The yellow reaction mixture is then stirred for a further 2 hours at 0°–5° C. 100 ml of 50% strength tetrafluoboric acid are then added and stirring is continued for 1 hour at the same temperature.

The precipitate is filtered off and washed with a copious amount of water. After having been dried in air, the diazonium tetrafluoborate (4.8 g) is heated in a two-neck flask equipped with a reflux condenser, under a gentle stream of nitrogen. The reaction commences at about 110° C. bath temperature. When the reaction has subsided, the bath temperature is raised to 200° C. for 15 minutes. When the mixture has cooled, the solids are purified by boiling three times in methanol, using 50 ml each time, and are filtered off hot. A further amount of the product crystallizes from the methanolic mother liquors.

In total, 3.2 g of cis,trans-5,6-dihydro-9-fluoro-morphanthridine-6,11-dione, of melting point 250°–254° C., are obtained.

(b) Further reaction to give the end product, by a method similar to Example 1:

cis,trans-9-Fluoro-11-cyanomethylene-5,6-dihydromorphanthridin-6-one is obtained by a method similar to Example 1b. Melting point 280°–285° C.

cis,trans-9-Fluoro-11-cyanomethylene-6-(4-methylpiperazin-1-yl)-morphanthridine is obtained by a method similar to Example 1a. Melting point 120°–125° C.

EXAMPLE 13

(a)

cis,trans-3-Methyl-11-cyanomethylene-6-(4-methylpiperazin-1-yl)-morphanthridine

The compound is prepared by a method similar to Example 1: yellow crystals of melting point 192°–200° C. The 3-position of the methyl group is established by X-ray structural analysis.

To separate the cis- and trans-isomers, the isomer mixture is subjected to fractional recrystallization from methanol. The first fraction obtained (thin layer of silica gel, 85/15 toluene/methanol) is highly enriched non-polar isomer, which is again recrystallized from methanol. X-ray structural analysis shows that this isomer, of melting point 224° C., is cis-3-methyl-11-cyanomethylene-6-(4-methyl-piperazin-1-yl)-morphanthridine.

The corresponding polar trans-isomer is best obtained by fractionally crystallizing the residue from the mother liquor, obtained above, from cyclohexane; the pure trans-3-methyl-11-cyanomethylene-6-(4-methylpiperazin-1-yl)-morphanthridine melts at 193°–195° C.

The starting material used is the ring enlargement product of 2-methyl-anthraquinone, prepared by the method of L. H. Werner et al., loc. cit., from which the more sparingly soluble fraction is isolated by fractional crystallization from toluene and recrystallization from dimethylformamide, giving 3-methyl-5,6-dihydromorphanthridine-6,11-dione, of melting point 259°–263° C.").

Carbonyl olefination gives cis,trans-3-methyl-11-cyanomethylene-5,6-dihydro-morphanthridine of melting point 233°–235° C.

(b)

cis,trans-2-Methyl-11-cyanomethylene-6-(4-methyl-piperazin-1-yl)-morphanthridine The compound is prepared by a method similar to Example 1. Yellow crystals of melting point 162°–164° C. The 2-position of the methyl group is established by X-ray structural analysis.

To separate the cis- and trans-isomers, the isomer mixture is subjected to fractional recrystallization from ethanol. The first fraction obtained (thin layer of silica gel, 85/15 toluene/methanol) is highly enriched polar isomer, which is again recrystallized from ethanol. X-ray structural analysis shows that this isomer, of melting point 183° C., is trans-2-methyl-11-cyanomethylene-6-(4-methyl-piperazin-1-yl)-morphanthridine.$\frac{1}{2}H_2O$.

The corresponding non-polar cis-isomer is best obtained by repeated column chromatography (silica gel, 98/2 methylene chloride/methanol as the migrating agent) of the residue of the mother liquors, obtained above: melting point 92°–95° C.

The starting material used is 2-methyl-5,6-dihydromorphanthridine-6,11-dione, of melting point 198°–202° C., obtained as the more readily toluene-soluble fraction (see Example 13a) and enriched by recrystallization from 1:2 dioxane/ethanol.

Further fractional crystallization of the dioxane/ethanol mother liquor makes it possible also to enrich one of the two residual isomers still present, namely 8- or 9-methyl-5,6-dihydro-morphanthridine-6,11-dione.

The carbonyl olefination gives cis,trans-2-methyl-11-cyanomethylene-5,6-dihydro-morphanthridin-6-one, of melting point 228°–230° C.

EXAMPLE 14 cis,trans-2-, 3-, 8- and 9-trifluoromethyl-11-cyanomethylene-6-(4-methyl-piperazin-1-yl)-morphanthridine.$\frac{1}{2}H_2O$.

The preparation of the starting material, 2-trifluoromethyl-anthraquinone, is described in German Pat. No. 713,745.

The ring enlargement to give the four isomers, namely 2-, 3-, 8- and 9-trifluoromethyl-5,6-dihydromorphanthridine-6,11-dione, is carried out by a method similar to Example 8a. Recrystallization from toluene gives the isomer mixture, of melting point 177°–179° C. The individual isomers can be enriched by fractional crystallization from ethanol. The compound which crystallizes in the greatest yield is a trifluoromethyl-5,6-dihydro-morphanthridine-6,11-dione isomer of melting point 230°–234° C.

Further conversion to the end product by a method similar to Example 1:

cis,trans-2-, 3-, 8- and 9-Trifluoromethyl-11-cyanomethylene-5,6-dihydro-morphanthridin-6-one isomer mixture, obtained by a method similar to Example 1b: melting point 130°–133° C.

cis,trans-2-, 3-, 8- and 9-Trifluoromethyl-11-cyanomethylene-6-(4-methyl-piperazin-1-yl)-morphanthridine isomer mixture, obtained by a method similar to Example 1a: melting point 93°–96° C.

EXAMPLE 15

It is to be emphasized at this point that in all the Examples described, the sequence of the carbonyl olefination and of the introduction of the piperazine radical into the 6-position can be successfully inverted, and in some cases this even has the advantage of increasing the yield. In this case, the corresponding 5,6-dihydro-morphanthridine-6,11-dione is used as the starting material and is converted to 6-chloro-morphanthridin-11-one by the method described by F. Hunziker et al., Helv. Chim. Acta 49 (1966), 1,433, and the latter is reacted with N-methylpiperazine, as described in the same publication, to give 6-(4-methyl-piperazin-1-yl)-morphanthridin-11-one. The Wittig-Horner carbonyl olefination is then carried out as described earlier.

In Examples 16 to 25, which follow, it is advantageous to employ this inverted reaction sequence.

EXAMPLE 16 cis,trans-11-Methylcarbonyl-methylene-6-(4-methyl-piperazin-1-yl)-morphanthridine.$H_2O$.

3.6 g (12 millimoles) of 6-(4-methyl-piperazin-1-yl)-morphanthridin-11-one are dissolved in 60 ml of dimethylformamide and the solution is stirred at room temperature under nitrogen. A mixture of 3.96 g (24 millimoles) of dimethyl 2-oxopropyl-phosphonate and 4.2 g (24 millimoles) of 30% strength solution of sodium ethylate in 15 mol of dimethylformamide is added dropwise and stirring is continued for from 10 to 14 hours at room temperature. The reaction mixture is then poured into ice-water and repeatedly extracted with methylene chloride. The combined organic phases are repeatedly washed with water and dried over sodium sulfate. They are concentrated, and the crude product obtained is purified by column chromatography (silica gel, 95/5 methylene chloride/methanol). 3.1 g (72%) of yellow crystals, of melting point 133°–136° C.

EXAMPLE 17 cis,trans-6-(4-Methyl-piperazin-1-yl)-11-thiomethyl-methylene-morphanthridine.½H$_2$O The compound is prepared by a method similar to Example 16, using diethyl methylmercapto-methyl-phosphonate (J. Shahak and J. Almog, Synthesis (1969), 170): colorless crystals of melting point 80°–86° C.

EXAMPLE 18 cis,trans-11-Benzylidene-6-(4-methyl-piperazin-1-yl)-morphanthridine

The compound is prepared by a method similar to Example 16, using diethyl benzyl-phosphonate: yellowish crystals of melting point 203°–220° C.

EXAMPLE 19 cis,trans-11-(o-Cyano)-benzylidene-6-(4-methyl-piperazin-1-yl)-morphanthridine

The compound is prepared by a method similar to Example 16, using diethyl (o-cyano)-benzyl-phosphonate: yellow crystals of melting point 225°–228° C.

EXAMPLE 20 cis,trans-11-Carboxamidomethylene-6-(4-methyl-piperazin-1-yl)-morphanthridine

The compound is prepared by a method similar to Example 16, with the following changes:
(a) 1 equivalent of diethyl phosphonoacetamide is first introduced into DMF,
(b) 1 equivalent of sodium hydride is added,
(c) 1 equivalent of 6-(4-methyl-piperazin-1-yl)-morphanthridin-11-one in DMF is added dropwise. A 73% yield of yellowish crystals, identical with the end product produced as described in Example 3, is obtained.

EXAMPLE 21 cis,trans-11-N-Methyl-carboxamidomethylene-6-(4-methylpiperazin-1-yl)-morphanthridine The compound is prepared by a method similar to Example 20, using diethyl N-methyl-phosphonoacetamide (prepared by an Arbuzov reaction from triethyl phosphite and N-methylchloroacetamide): yellow crystals of melting point 111°–117° C., identical with the end product obtained as described in Example 4.

EXAMPLE 22 cis,trans-11-N,N-Dimethyl-carboxamidomethylene-6-(4-methyl-piperazin-1-yl)-morphanthridine.H$_2$O The compound is prepared by a method similar to Example 20, using diethyl N,N-dimethyl-phosphonoacetamide (prepared by an Arbuzov reaction from triethyl phosphite and N,N-dimethyl-chloroacetamide): yellow crystals of melting point 161°–163° C., identical with the end product obtained as described in Example 5.

EXAMPLE 23 cis,trans-11-N-Isopropyl-carboxamidomethylene-6-(4-methyl-piperazin-1-yl)-morphanthridine The compound is prepared by a method similar to Example 20, using diethyl N-isopropyl-phosphonoacetamide (prepared by an Arbuzov reaction from triethyl phosphite and N-isopropyl-chloroacetamide), the temperature being raised to 60°–90° C. during the subsequent period of stirring of 5–12 hours: yellow crystals of melting point 100°–103° C.

EXAMPLE 24 cis,trans-11-N,N-Diethyl-carboxamidomethylene-6-(4-methyl-piperazin-1-yl)-morphanthridine The compound is prepared by a method similar to Example 23, using diethyl N,N-diethyl-phosphonoacetamide (prepared by an Arbuzov reaction from triethyl phosphite and N,N-diethyl-chloroacetamide): yellow crystals of melting point 123°–129° C.

EXAMPLE 25 cis,trans-11-(Piperidin-1-yl-carbonyl)-methylene-6-(4-methyl-piperazin-1-yl)-morphanthridine.H$_2$O The compound is prepared by a method similar to Example 20, using diethyl N,N-pentamethylene-phosphonoacetamide (prepared by an Arbuzov reaction from triethylphosphite and N,N-pentamethylene-chloroacetamide), the temperature being raised to 50°–80° C. during the subsequent period of stirring of 5–10 hours: yellowish crystals of melting point 226°–227° C.

EXAMPLE 26 cis,trans-11-(α-Methoxy)-cyanomethylene-6-(4-methyl-piperazin-1-yl)-morphanthridine.1.5H$_2$O The compound is prepared by a method similar to Example 20, using diethyl cyano-(methoxy)-methyl-phosphonate (S. E. Dinizo et al., J. Org. Chem. 41 (1976), 2,846), the temperature being raised to 50°–80° C. during the subsequent period of stirring of 5–10 hours: yellow crystals of melting point 82°–85° C.

EXAMPLE 27 cis,trans-6-(4-Methyl-piperazin-1-yl)-11-methylsulfonylmethylene-morphanthridine The compound is prepared by a method similar to Example 16, using diethyl methylsulfonyl-methyl-phosphonate (I. Shahak and J. Almog, Synthesis (1969), 170): yellow crystals of melting point 99°–104° C.

EXAMPLE 28 cis,trans-6-(4-Methyl-piperazin-1-yl)-11-pyrid-4-yl-methylene-morphanthridine.0.75H$_2$O The compound is prepared by a method similar to Example 20, using diethyl picol-4-yl-phosphonate (E. Maruszewska et al., Roczniki Chem. 38 (1964), 625), the temperature being raised to 50°–90° C. during the subsequent period of stirring of 5–10 hours: yellowish crystals of melting point 272°–275° C.

EXAMPLES 29 TO 66

General procedure for the preparation of the compounds 29 to 66, for by introducing the various nucleophilic alkylamino or alkoxy radicals A into the 6-position of the 6-chloro-morphanthridine derivatives.

The 6-chloro-morphanthridine derivative is mixed with from 2 to 5 equivalents of the alkylamine or aminoalkanol AH and the mixture is heated at 110° C. under nitrogen for from 3 to 5 hours. Where the nucleophilic agent AH is volatile, the excess thereof is then distilled off under reduced pressure. In such cases, the residue is then taken up in ice water and repeatedly extracted with methylene chloride; where the nucleophilic agent is not volatile, the entire reaction mixture is taken up in ice water and extracted repeatedly with methylene chloride. The combined methylene chloride phases are then washed with water, dried and concentrated. The crude product which remains is either recrystallized from ethanol in the presence of active charcoal or (especially where alkylamines of relatively high molecular weight are present) is purified by column chromatography over silica gel, using 95/5 methylene chloride/methanol.

The following are examples of compounds of the formula I prepared by the above general method:

29. cis,trans-11-Cyanomethylene-6-(4-β-hydroxyethyl-piperazin-1-yl)-morphanthridine.½H$_2$O, melting point 111°-113° C.
30. cis,trans-11-Cyanomethylene-6-piperazin-1-yl-morphanthridine.H$_2$O, melting point 208°-211° C.
31. cis,trans-11-Cyanomethylene-6-(4-ethyl-piperazin-1-yl)-morphanthridine, melting point 86°-90° C.

Separation of the cis- and trans-11-cyanomethylene-6-(4-ethyl-piperazin-1-yl)-morphanthridine isomers: to separate the cis- and trans-isomers, the isomer mixture is subjected to fractional recrystallization from methanol. The less soluble fraction, which crystallizes out first, is the trans-isomer (the polar component on a silica gel thin layer plate, using 85/15 toluene/methanol as the migrating agent). Recrystallization from ethanol gives the pure trans-isomer, of melting point 181°-183° C.

Column chromatography over silica gel, using 95/5 methylene chloride/methanol, gives the less polar cis-isomer in a purified form, of melting point 138°-140° C.

32. cis,trans-11-Cyanomethylene-6-homopiperazin-1-yl-morphanthridine.HCl.H$_2$O, melting point 175°-178° C.
33. cis,trans-11-Cyanomethylene-6-(2-dimethylaminoethylamino)-morphanthridine.½H$_2$O, melting point 76°-79° C.
34. cis,trans-11-Cyanomethylene-6-(2-aminoethylamino)morphanthridine.½H$_2$O, melting point 86°-90° C.
35. cis,trans-11-Cyanomethylene-6-bis-(β-hydroxyethyl)amino-morphanthridine.½H$_2$O, melting point 93°-95° C.
36. cis,trans-11-Cyanomethylene-6-(2-morpholin-1-yl-ethylamino)-morphanthridine, melting point 89°-91° C.
37. cis,trans-11-Cyanomethylene-6-(2-piperazin-1-yl-ethylamino)-morphanthridine.H$_2$O, melting point 98°-104° C.
38. cis,trans-11-Cyanomethylene-6-(2-piperidin-1-yl-ethylamino)-morphanthridine.½H$_2$O, melting point 83°-85° C.

Separation of the cis- and trans-11-cyanomethylene-6-(2-piperidin-1-yl-ethylamino)-morphanthridine isomers: the cis- and trans-isomers can be separated by column chromatography over silica gel, using 95/5 methylene chloride/methanol. The cis-isomer (the nonpolar component on a silica gel thin layer plate, using 85/15 toluene/methanol as the migrating agent) is obtained in the form of yellowish crystals of melting point 76°-78° C., whilst the more polar trans-isomer melts at 103°-106° C.

39. cis,trans-11-Cyanomethylene-6-(1-methyl-2-morpholin-1-yl-ethylamino)-morphanthridine, melting point 80°-85° C.
40. cis,trans-11-Cyanomethylene-6-[1-methyl-2-(4-methyl-piperazin-1-yl)-ethylamino]-morphanthridine.H$_2$O, melting point 99°-104° C.
41. cis,trans-11-Cyanomethylene-6-morpholin-1-yl-morphanthridine, melting point 181°-185° C.
42. cis,trans-11-Cyanomethylene-6-(N'-methyl-piperidin-4-yl-amino)-morphanthridine.½H$_2$O, melting point 132°-134° C.
43. cis,trans-11-Cyanomethylene-6-(4-methyl-piperidin-1-yl)-morphanthridine, melting point 145°-148° C.
44. cis,trans-11-Cyanomethylene-6-(4-hydroxy-piperidin-1-yl)-morphanthridine.H$_2$O, melting point 105°-108° C.
45. cis,trans-11-Cyanomethylene-6-(3-dimethylaminopropylamino)-morphanthridine.0.3H$_2$O, melting point 70°-72° C.
46. cis,trans-11-Cyanomethylene-6-N-methyl-(1-methyl-piperidin-4-yl)-amino-morphanthridine.0.3-H$_2$O, melting point 105°-107° C.
47. cis,trans-11-Cyanomethylene-6-(2-dimethylaminoethoxy)-morphanthridine.½H$_2$O, melting point 51°-53° C.
48. cis,trans-11-Cyanomethylene-6-(3-dimethylaminopropoxy)-morphanthridine.H$_2$O, melting point 54°-56° C.
49. cis,trans-11-Cyanomethylene-6-(2-piperidin-1-yl-ethoxy)-morphanthridine.½H$_2$O, melting point 67°-70° C.
50. cis,trans-11-Cyanomethylene-6-(1-methyl-piperidin-4-yl-oxy)-morphanthridine.½H$_2$O, melting point 80°-85° C.

In addition to the above main product of the reaction of 6-chloromorphanthridine with 4-hydroxy-1-methyl-piperidine, cis,trans-11-cyanomethylene-6-(4-hydroxy-piperidin-1-yl)-morphanthridine.H$_2$O, of melting point 105°-108° C., was isolated as a by-product when carrying out column chromatography.

51. cis,trans-11-Cyanomethylene-6-(2-diethylaminoethylamino)-morphanthridine.H$_2$O, melting point 84°-90° C.
52. cis,trans-11-Cyanomethylene-6-(3-diethylaminopropylamino)-morphanthridine.½H$_2$O, melting point 103°-105° C.
53. cis,trans-11-Cyanomethylene-6-(4-dimethylamino-n-butylamino)-morphanthridine.1.5 HCl, melting point 125°-129° C.
54. cis,trans-11-Cyanomethylene-6-(2-pyrrolidin-1-yl-ethylamino)-morphanthridine.0.75H$_2$O, melting point 84°-88° C.
55. cis,trans-11-Cyanomethylene-6-(3-piperidin-1-yl-propylamino)-morphanthridine.0.75H$_2$O, melting point 80°-85° C.

56. cis,trans-11-Cyanomethylene-6-(N-ethylpyrrolidin-2-yl-methylamino)-morphanthridine.0.25H$_2$O, melting point 75°-79° C.
57. cis,trans-11-Cyanomethylene-6-[2-(4-methylpiperazin-1-yl]-ethylamino)-morphanthridine.0.75-H$_2$O, melting point 89°-92° C.
58. cis,trans-11-Cyanomethylene-6-[3-(4-methylpiperazin-1-yl]-propylamino)-morphanthridine.H$_2$O, melting point 80°-85° C.
59. cis,trans-11-Cyanomethylene-6-(2-phenylamino-ethylamino)-morphanthridine.0.25H$_2$O, melting point 95°-100° C.
60. cis,trans-11-Cyanomethylene-6-(2-dimethylaminoethyl-N-methyl-amino)-morphanthridine.0.75H$_2$O, melting point 65°-67° C.
61. cis,trans-11-Cyanomethylene-6-[2-(N-methyl-N-benzyl-amino)-ethylamino]-morphanthridine.0.25-H$_2$O, melting point 65°-72° C.
62. cis,trans-11-Cyanomethylene-6-[3-(N-methyl-N-benzyl-amino)-propylamino]-morphanthridine.0.25H$_2$O, melting point 59°-61° C.
63. cis,trans-11-Cyanomethylene-6-(N'-methyl-homopiperazin-1-yl)-morphanthridine.0.75H$_2$O, melting point 73°-80° C.
64. cis,trans-11-Cyanomethylene-6-(N-methyl-piperidin-3-yl-methoxy)-morphanthridine.H$_2$O, melting point 93°-95° C.
65. cis,trans-11-Cyanomethylene-6-(N-methyl-piperidin-2-yl-methoxy)-morphanthridine, melting point 67°-70° C.
66. cis,trans-11-Cyanomethylene-6-(N-methyl-piperidin-3-yl-methylamino)-morphanthridine.H$_2$O, melting point 110°-114° C.

EXAMPLE 67

(a)

cis,trans-11-Cyanomethylene-6-(4-methyl-4-oxypiperazin-1-yl)-morphanthridine.2H$_2$O 3.0 g (9.1 millimoles) of cis,trans-11-cyanomethylene-6-(4-methyl-piperazin-1-yl)-morphanthridine are dissolved in 100 ml of hot ethanol and 1.5 ml of 30% strength hydrogen peroxide are added. The mixture is refluxed for 5 hours, and the excess hydrogen peroxide is then destroyed by dropping a small sheet of platinum into the reaction mixture and refluxing for a further 2 hours. The reaction mixture is then filtered, the filtrate is evaporated and the resulting N-oxide is purified by column chromatography over silica gel, using 95/5 methylene chloride/methanol as the migrating agent. 2.5 g (80%) of yellow crystals of melting point 141°-148° C. are obtained.

To separate the cis- and trans-isomers, the isomer mixture is subjected to fractional recrystallization from a small amount of methylene chloride. The first fraction isolated is highly enriched non-polar isomer (according to a thin layer chromatogram on silica gel, using 85/15 toluene/methanol), and is recrystallized from a small amount of ethanol. By analogy to the cis,trans-isomer analyses described above, this isomer, of melting point 241° C., is taken to belong to the cis-series.

The corresponding polar trans-isomer, of melting point 169° C., is obtained by column chromatography over silica gel, using 95/5 methylene chloride/methanol as the migrating agent, of the residue of the mother liquor, obtained above.

Advantageously, both isomers are prepared directly by oxidizing, respectively, the cis- and trans-11-cyanomethylene-6-(4-methyl-piperazin-1-yl)-morphanthridines (prepared, and separated, as described in Example 1) by the method described above; no cis,trans-isomerization occurs during the oxidation.

The following are prepared by a similar method, starting from the corresponding 6-amino-11-cyanomethylenemorphanthridines (Examples 29 and 13)

(b) cis,trans-11-Cyanomethylene-6-(4-β-hydroxyethyl-4-oxy-piperazin-1-yl)-morphanthridine.1.5H$_2$O, melting point 144°-146° C., (c) cis,trans-11-Cyanomethylene-2-methyl-6-(4-methyl-4-oxy-piperazin-1-yl)-morphanthridine.2.25-H$_2$O, melting point 165°-166° C., (d) cis,trans-11-Cyanomethylene-3-methyl-6-(4-methyl-4-oxy-piperazin-1-yl)-morphanthridine.2.5H$_2$O, melting point 162° C. (with decomposition) and (e) cis,trans-11-Cyanomethylene-6-(N-methyl-N-oxypiperidin-3-yl-methoxy)-morphanthridine, melting point 105°-108° C. (with decomposition).

Examples of formulations prepared by conventional methods:

| 1. | Tablets | |
|---|---|---|
| (a) | An active compound of the formula I | 5 mg |
| | Lactose | 200 mg |
| | Methylcellulose | 15 mg |
| | Corn starch | 50 mg |
| | Talc | 11 mg |
| | Magnesium stearate | 4 mg |
| | | 285 mg |
| (b) | An active compound of the formula I | 20 mg |
| | Lactose | 178 mg |
| | Avicel | 80 mg |
| | Polywachs 6000 | 20 mg |
| | Magnesium stearate | 2 mg |
| | | 300 mg |
| (c) | An active compound of the formula I | 50 mg |
| | Polyvinylpyrrolidone (mean molecular weight 25,000) | 170 mg |
| | Polyethylene glycol (mean molecular weight 4,000) | 14 mg |
| | Hydroxypropylmethylcellulose | 40 mg |
| | Talc | 4 mg |
| | Magnesium stearate | 2 mg |
| | | 280 mg |

The active compound is moistened with a 10% strength aqueous solution of the polyvinylpyrrolidone and the mixture is forced through a sieve of 1.0 mm mesh size and dried at 50° C. These granules are mixed with polyethylene glycol (mean molecular weight 4,000), hydroxypropylmethylcellulose, talc and magnesium stearate, and tablets weighing 280 mg are pressed from the mixture.

| 2. | Example of dragees | |
|---|---|---|
| | A compound of the formula I | 3 mg |
| | Lactose | 90 mg |
| | Corn starch | 60 mg |
| | Polyvinylpyrrolidone | 6 mg |
| | Magnesium stearate | 1 mg |
| | | 160 mg |

A mixture of the active compound with lactose and corn starch is moistened with an 8% strength aqueous solution of the polyvinylpyrrolidone and granulated by forcing it through a 1.5 mm sieve, after which it is dried at 50° C. and forced through a 1.0 mm sieve. The granules thus obtained are mixed with magnesium stearate and molded to form dragee cores. These are provided with a coating, essentially consisting of sugar and talc, by a conventional method.

| 3. | Capsule formation | |
|---|---|---|
| | A compound of the formula I | 5.0 mg |
| | Magnesium stearate | 2.0 mg |
| | Lactose | 19.3 mg |
| 4. | Injection solution | |
| | A compound of the formula I | 10 mg |
| | Sodium chloride | 9 mg |
| | Distilled water, q.s. to make up to 1.0 ml | |

We claim:
1. A compound of the formula I

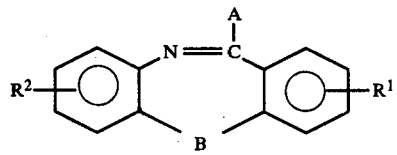

where $R^1$ and $R^2$ are hydrogen, fluorine, chlorine, methyl or trifluoromethyl and A is 4-methyl-piperazin-1-yl, 4-ethyl-piperazin-1-yl, 4-methyl-4-oxy-piperazin-1-yl, N'-methyl-homopiperazin-1-yl or 2-piperidin-1-yl-ethyl-amino and where B is an alkylene group of the formula

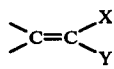

where X is hydrogen, and Y is cyano.

2. A compound of the formula I as set forth in claim 1, where $R^1$ and $R^2$ are hydrogen or methyl, the amino radical

representing A is 4-methyl-piperazin-1-yl, 4-ethyl-piperazin-1-yl, 4-methyl-4-oxy-piperazin-1-yl, N'-methyl-homopiperazin-1-yl or 2-piperidin-1-yl-ethylamino and, in the alkylene radical B, X is hydrogen and Y is cyano.

3. cis,trans-11-Cyanomethylene-6-(4-methylpiperazin-1-yl)-morphanthridine.

4. cis-11-Cyanomethylene-6-(4-methyl-piperazin-1-yl)-morphanthridine.

5. trans-11-Cyanomethylene-6-(4-methyl-piperazin-1-yl)-morphanthridine.

6. cis,trans-11-Cyanomethylene-6-(4-methyl-4-oxypiperazin-1-yl)-morphanthridine.

7. cis-11-Cyanomethylene-6-(4-methyl-4-oxypiperazin-1-yl)-morphanthridine.

8. trans-11-Cyanomethylene-6-(4-methyl-4-oxypiperazin-1-yl)-morphanthridine.

9. cis,trans-11-Cyanomethylene-2-methyl-6-(4-methyl-piperazin-1-yl)-morphanthridine.

10. cis,trans-11-Cyanomethylene-3-methyl-6-(4-methyl-piperazin-1-yl)-morphanthridine.

11. cis-11-Cyanomethylene-3-methyl-6-(4-methylpiperazin-1-yl)-morphanthridine.

12. trans-11-Cyanomethylene-3-methyl-6-(4-methyl-piperazin-1-yl)-morphanthridine.

13. cis,trans-11-Cyanomethylene-6-(4-ethyl-piperazin-1-yl)-morphanthridine.

14. trans-11-Cyanomethylene-6-(4-ethyl-piperazin-1-yl)-morphanthridine.

15. cis,trans-11-Cyanomethylene-6-(N'-methyl-homopiperazin-1-yl)-morphanthridine.

16. cis,trans-11-Cyanomethylene-6-(2-piperidin-1-yl-ethyl-amino)-morphanthridine.

* * * * *